United States Patent [19]

Ostendorf

[11] Patent Number: 5,720,966
[45] Date of Patent: Feb. 24, 1998

[54] MEDICATED TISSUE PAPER PRODUCT

[75] Inventor: Ward W. Ostendorf, West Chester, Ohio

[73] Assignee: The Procter & Gamble Company, Cincinnati, Ohio

[21] Appl. No.: 590,070

[22] Filed: Jan. 17, 1996

Related U.S. Application Data

[63] Continuation-in-part of Ser. No. 358,862, Dec. 19, 1994, abandoned.

[51] Int. Cl.$^6$ .................. A01N 25/34; B32B 29/00
[52] U.S. Cl. ............. 424/402; 424/404; 428/537.5
[58] Field of Search .................. 424/402, 404; 428/537.5

[56] References Cited

U.S. PATENT DOCUMENTS

| | | |
|---|---|---|
| 233,954 | 2/1880 | Thompson . |
| 249,553 | 11/1881 | Snyder . |
| 433,827 | 8/1890 | Schultz . |
| 904,287 | 11/1908 | Warham . |
| 967,688 | 8/1910 | Titherley . |
| 1,617,822 | 2/1927 | O'Leary . |
| 2,933,431 | 4/1960 | Sperouleas . |
| 3,325,003 | 6/1967 | Bilezerian . |
| 3,619,280 | 11/1971 | Scheuer . |
| 3,814,096 | 6/1974 | Weiss et al. . |
| 3,818,533 | 6/1974 | Scheuer . |
| 3,896,807 | 7/1975 | Buchalter . |
| 3,900,671 | 8/1975 | Evans . |
| 4,069,345 | 1/1978 | Gascoyne et al. . |
| 4,112,167 | 9/1978 | Dake et al. . |
| 4,136,163 | 1/1979 | Watson et al. . |
| 4,190,643 | 2/1980 | Watson et al. . |
| 4,343,783 | 8/1982 | Hooper et al. . |
| 4,426,418 | 1/1984 | Coleman et al. ............ 428/211 |
| 4,458,810 | 7/1984 | Mahoney . |
| 4,471,871 | 9/1984 | Rockliffe et al. . |
| 4,481,243 | 11/1984 | Allen . |
| 4,752,496 | 6/1988 | Fellows et al. . |
| 4,786,367 | 11/1988 | Bogart et al. . |
| 4,806,418 | 2/1989 | Sigl . |
| 4,814,335 | 3/1989 | Kim ............................. 514/257 |
| 4,882,221 | 11/1989 | Bogart et al. ............. 428/308.8 |
| 5,143,900 | 9/1992 | Steltenkampeim ........... 512/26 |
| 5,256,417 | 10/1993 | Koltisk ......................... 424/402 |
| B1 3,814,096 | 10/1988 | Weiss et al. . |

FOREIGN PATENT DOCUMENTS 2066661  12/1980  United Kingdom .

OTHER PUBLICATIONS

Paper and Board Specialties, Abtract No. 6155–66, p. 600 Abstract 6159 –Fuhrer.

*Primary Examiner*—Helen Lee
*Attorney, Agent, or Firm*—Dinsmore & Shohl LLP

[57] ABSTRACT

A medicated, lotioned tissue paper includes a substrate and a semisolid therapeutic substance carried by the substrate. In a preferred application, the therapeutic substance is a lotion for soothing irritated and sore nasal areas and for providing improved delivery of a medicinal component to a user for relief of cold and allergy symptoms. The medicinal component is evenly dispersed into the lotion or contained in microcapsules which are substantially evenly dispersed into the lotion for controlled release of the medicinal component. The medicinal component may be a medicinal scent.

17 Claims, 2 Drawing Sheets

MEDICATED TISSUE PAPER PRODUCT

This is a continuation of application Ser. No. 08/358,862, filed Dec. 19, 1994, now abandoned.

TECHNICAL FIELD

This invention relates to medicated tissue paper, and in particular, to a facial tissue including a semisolid lotion with an encapsulated medicinal component or a liquid medicinal component mixed into the semisolid lotion for soothing skin and relieving cold symptoms, where the medicinal component may be a medicinal scent.

BACKGROUND ART

It is well known that facial tissue has been designed for strength, absorbency, and softness in order to absorb and contain large amounts of nasal discharge and other materials while limiting the amount of irritation, inflammation and soreness in the nasal area. Treated tissues also have been developed in an attempt to alleviate cold and allergy symptoms including sneezing, runny nose, and congestion. For example, lotioned tissue paper has been developed by impregnating the paper with an emollient or cream and is known to help reduce redness, irritation and soreness associated with frequent nose blowing and wiping during a cold or an allergy attack.

Tissues which are impregnated with an emollient are well known for their soothing effects on dry or irritated skin. Tissue also has been impregnated with a cream formulation which, upon the addition of moisture, forms a skin-soothing cream. Facial tissues impregnated with a liquid emollient, in contrast to cream emollient, also have been disclosed for soothing irritated skin. A disadvantage of existing lotioned tissues is that the tissues are fully impregnated over substantially their complete cross-sectional area with lotion such that the amount of lotion is not economized.

Scented tissues also are known in the prior art and several methods have been employed to distribute various scents on tissues. For example, it is known to impregnate, coat or spray tissues with scent, and/or to provide scent carrying material between one or more layers of tissues, so that the scent permeates each individual tissue.

There are, however, several disadvantages associated with well known scented tissues. For example, tissues impregnated or coated with scent generally lose their odor quickly because the scent dissipates during the shelf life of the tissues. Even if scent should remain relatively available until the tissues are purchased, once the box is opened for use, the remaining scent dissipates even more quickly. In order to address these problems, special resealable tissue containers were designed to help retain scent; however, such containers generally are expensive and inconvenient due to the necessity of resealing the box. In addition, scent that is applied directly to tissues generally does not transfer in use; thus, the scent is available to the user only while the tissue remains near the user's nose.

The prior art generally has employed liquid carriers, such as oils, for scents. While incidentally providing some softening benefits, oil lubricated tissues primarily provide a carrier for applying and retaining the scent on the tissue. Oil carriers allow for more even distribution of a scent on the tissue; however, the scent often separates from the oil carrier after application to the tissue. During use of the tissue, the scent, having separated from the carrier, generally does not transfer with the oil to the user's nasal area, and thus, the tissue does not provide lasting scent benefits. This is a disadvantage particularly for medicated tissues which provide analgesic benefits for cold or allergy relief. In addition, common oil carriers are not suitable for use with highly volatile scent compounds such as menthol type scents.

While tissues impregnated or coated with scented lotion can provide softening benefits, as mentioned above, they often lose their desirable odor during the pre-use shelf life of the tissues. Consequently, there is a continuing need for a treated tissue that can provide improved delivery of application treatments such as medicinal scent to a user for cold and allergy relief, soothing emollient effects to irritated nasal areas, improved shelf life of the tissue product, and economization of treatment materials. The terms "medicated" and "medicine" will be used broadly to connote the inclusion of any of a variety of application treatments including lotions, medicines, anti-bacterial agents, scents, salves and other therapeutic substances which might be desirable on tissues as discussed herein.

Accordingly, it is an object of the present invention to provide a medicated tissue which eliminates the problems of prior medicated tissues by providing a source of lotion containing a medicinal component to effectively alleviate cold symptoms and soothe irritated skin; to provide an improved means of delivering medicine to a user; to provide a more stable carrier for highly volatile medicinal compounds such as menthol in order to extend the product's shelf life; to provide even distribution of the medicinal component on the tissue; and to economize the amount of lotion required.

SUMMARY OF THE INVENTION

The present invention relates to a medicated tissue comprising, in a preferred embodiment, a substrate and a semisolid therapeutic substance carried by the substrate. The therapeutic substance comprises a lotion and a medicinal component dispersed throughout the lotion. The medicinal component, usually in liquid form, may be substantially dispersed directly into the lotion, or contained within microcapsules that are substantially dispersed into the lotion. Ultimately, the therapeutic substance is distributed during use of the tissue to the user's nasal area to provide soothing relief and for prolonging the user's exposure to the medicinal component which provides relief of cold and allergy symptoms. The medicinal component can be a medicine or a substance having a medicinal scent.

The substrate preferably comprises at least two plies of tissue paper which are connected only along patterns of embossments extending along the opposite longitudinal edges of the substrate. The therapeutic substance is distributed over a major portion of at least one surface of the substrate, but the region containing the embossments is left substantially free of therapeutic substance.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
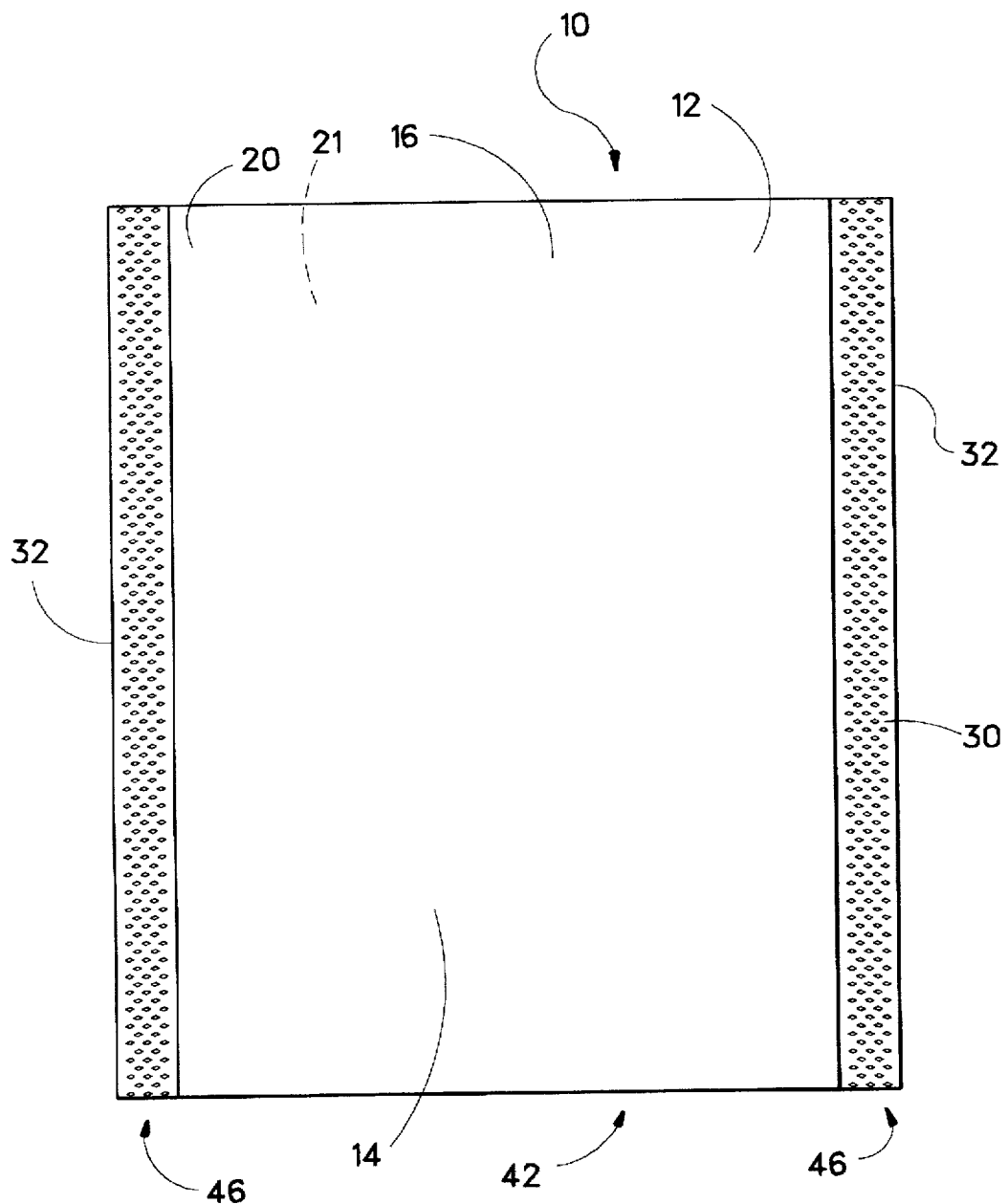
FIG. 1 is a plan view of a medicated tissue made in accordance with this invention.

Referring now to the drawings in detail, wherein like numerals indicate the same elements throughout the views, FIG. 1 illustrates a preferred embodiment of a medicated tissue of the present invention. The medicated tissue (10), preferably is a strong, and absorbent tissue paper having pleasant tactility and designed to provide relief of common cold and allergy symptoms as well as to provide relief to a sore and irritated nose and nasal area. Tissue (10) is illustrated as comprising two primary elements: a substrate (12) and a therapeutic substance (14) which is carried by the substrate (12). Each element will be discussed in turn.

Substrate (12) preferably can be the same as the tissue structure described in U.S. Pat. No. 4,481,243 by Allen, the disclosure of which is hereby incorporated by reference. Substrate (12) preferably is formed of a planar material commonly known as tissue paper and comprises two or more thin plies (e.g., 16, 18) of tissue paper. As a relatively thin planar material, substrate (12) will have two major surfaces, a front major surface (20) and a back major surface (21). At least one major surface (e.g., 20 or 21) must be soft and smooth for contacting a user's skin.

Substrate (12) must have pleasant tactility, meaning that it is soft, smooth, and pleasant to touch. In addition to tactility, substrate (12) must possess sufficient strength to allow it to accomplish its intended task. For example, for facial tissues, substrate (12) must have sufficient tensile strength throughout, in both the wet and dry states, to maintain its physical integrity during nose blowing and wiping procedures. In common facial tissue applications, it is preferred that substrate (12) have a total tensile strength of at least about 235 grams per centimeter in the dry state ("total tensile strength" is the sum of the tensile strengths of substrate (12) as measured in the machine direction, "MD", and in the cross machine direction. "CD", by standard measuring techniques). Substrate (12) also should have a minimum CD tensile strength in the wet state of at least about 20 grams per centimeter. Preferably, substrate (12) for facial tissue (10) will have a dry total tensile strength of at least about 315 grams per centimeter and a wet CD tensile strength of at least about 40 grams per centimeter.

In addition to pleasant tactility and strength, substrate (12) generally must be absorbent for many common applications. For example, a substrate that absorbs at least about five grams of water per gram of substrate generally will possess adequate absorbency for facial tissue products and will reduce the number of times the substrate must be rubbed or passed across the nose to absorb nasal discharge.

Figure 3:
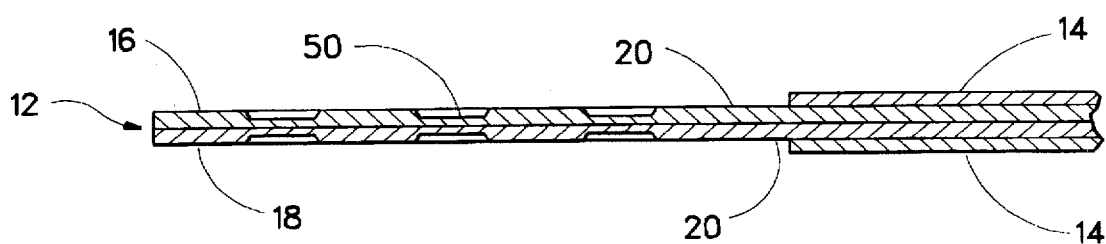
FIG. 3 is a cross sectional view of a portion of the medicated tissue of FIG. 2, taken along line 3—3 thereof, illustrating a preferred arrangement of embossments used in connecting the plies of the tissue.

In general, any planar tissue paper material meeting the requirements of pleasant tactility, strength, and absorbency can be used in the substrate of medicated tissue (10) of this invention. As shown in FIG. 3, substrate (12) preferably comprises at least two plies (16, 18) of tissue paper, which can be identical to one another or different. While a substrate comprising two plies of tissue paper is a preferred embodiment, it is to be understood that substrates comprising three or more plies also are suitable for use in the present invention.

In substrate (12), various plies (16, 18) preferably are connected in coextensive and adjacent relation by appropriate means for laminating the individual structures. The laminating means can be an embossing means, such as those known to those skilled in the art. Preferably, plies (16, 18) are laminated by mechanical embossing and without the use of adhesives, such as by a pattern of embossments (30) extending along longitudinal edges (32) of substrate (12). When the substrate consists of two or more tissue paper plies (16, 18), the plies preferably are free to move with respect to one another except in the region of the pattern of embossments (30). The preferred pattern of embossments (30) is described with particularity hereinafter.

Figure 4:
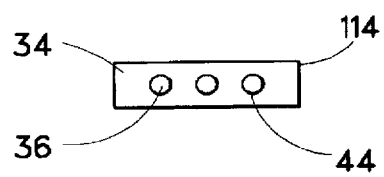
FIG. 4 is an enlarged view of a potion of an alternative embodiment of the therapeutic substance layer of FIG. 3.

Referring to FIG. 4, the second primary element of the present invention is a semisolid therapeutic substance (14), which preferably comprises a lotion (34) and a medicinal component (36). For example, the therapeutic substance might advantageously comprise about 50% to about 99.75% lotion (34) and about 0.25% to about 50% medicinal component (36). Lotion (34) softens, soothes, supples, coats, lubricates, or moisturizes the skin, and simultaneously permits medicinal scent (36) to transfer to the user along with the lotion in order to provide prolonged relief from cold and allergy symptoms. In choosing lotions, those skilled in the art can readily select compositions which do not deleteriously interact with the substrate, are economical to use, are safe for use on human skin, can be conveniently applied to the substrate, and are easily released from the substrate and transferred to the skin by the simple act of wiping the medicated tissue across the skin (or during common nose blowing procedures).

There are many suitable lotions that may be readily selected by one skilled in the art such as the emollients described in U.S. Pat. No. 4,481,243 to Allen. However, a preferred lotion composition is semisolid at 20° C. (i.e., ambient temperatures) and has a rheology typical of pseudo plastic or plastic fluids. Since the preferred semisolid lotion composition contains both solid and liquid components, it can have the appearance of a semisolid, but can be made to flow by the application of shear forces. A lotion which remains semisolid at ambient temperatures does not tend to migrate or separate and flow into the interior of the tissue substrate to which it is applied. This characteristic allows optimization and economization of the volume of therapeutic substance required for an effective product, reduces the likelihood that the medicine will volatilize, and ensures that the therapeutic substance is readily available for transfer to the user. A preferred composition for the lotion which provides these desired characteristics comprises by weight from about 40% to about 60% mineral oil, from about 6% to about 14% paraffin wax, from about 15% to about 25% cetearyl alcohol (a mixture of fatty alcohols consisting predominately of cetyl and steryl alcohols), from about 1% to about 5% aloe extract, and from about 5% to about 14% steareth-2 (polyethyleneglycol ethers of steryl alcohol which conform to the formula: $CH_3(CH_2)_{16}CH_2(OCH_2CH_2)OH$, where n has an average value of 2.)

As mentioned previously, the therapeutic substance (14) of the present invention preferably also comprises a medicinal component (36). Those skilled in the art may select medicinal components that provide efficacious results; however, preferred medicinal components include medicinal scents such as natural menthol, synthetic menthol, and camphor (these scents are collectively referred to herein as "medicinal scent" or "medicinal scents"), as well as medicines like viricides, disinfectants, analgesics, and other types of medicine having suitable medicinal properties. An exemplary mentholated medicinal scent is an ointment which is sold under the trademark "VICKS VAPORUB"®.

There are two preferred methods of distributing one or more medicinal components (36) throughout lotion (34). A first method is a pure method embodiment wherein a liquid medicinal component (36) is blended directly into lotion (34) such that the medicinal component is transferred with the lotion in use to the user's nasal area for prolonged exposure to the medicinal properties. The second method is an encapsulation method embodiment (illustrated as 114 in FIG. 3) whereby the medicinal component (36) is contained in microcapsules (44) which are mixed with the lotion (34). The encapsulation method embodiment (114) can provide a controlled release of the medicinal component (36) which further prolongs the shelf life of the medicinal component as well as similarly extending the user's exposure to the medicinal component (36) after transfer to the skin. Lotion (34) holds microcapsules (44) on substrate (12) prior to transfer, and functions as a protective lubricant after transfer to prevent the microcapsules (44) from irritating the skin.

There are several well known types of encapsulation that may be selected by one skilled in the art to provide for the controlled release of scent in the present invention. For example, two suitable types of encapsulation include: (a) microcapsules that rupture at the point of use so that the medicinal component is transferred to the user, and (b) microcapsules that continually effuse the medicinal component without rupturing. Microcapsules that rupture at the point of use provide improved cold and allergy relief and shelf life, because the medicinal component generally cannot be dissipated until the microcapsule ruptures when the therapeutic substance is transferred onto the user's nasal area. Microcapsules that continually effuse medicinal component without rupturing also provide improved cold and allergy relief and shelf life, because the medicinal component is retained within partially open microcapsules which allows the medicinal component to continually effuse over a predetermined time period. The medicinal component in this type of capsule dissipates at a controlled, generally more uniform rate and provides continual, longer lasting, and more reliable or defined benefits to the user. As will be understood by those skilled in the encapsulation art, suitable encapsulation technologies include coacervation, prilling, microsponging, and spray drying. Examples of preferred specific encapsulation products include those sold under the name Polyiff, as available from International Flavor and Fragrances, and IN-CAP, as available from Polak Frutal Works.

Figure 2:
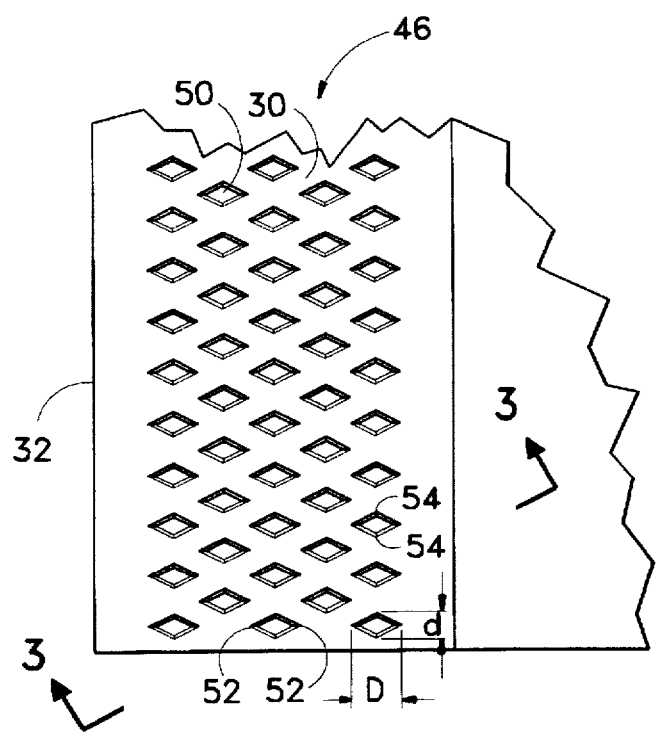
FIG. 2 is an enlarged partial view of a portion of the medicated tissue shown in FIG. 1 illustrating an embossing region.

Therapeutic substance (14) can be applied to substrate (12) by any convenient technique such as spraying, dipping, padding, or, in the case of the preferred lotion and other substances having similar physical properties, by extrusion of the melted lotion onto substrate (12). The therapeutic substance (14) preferably is applied at least to the soft, smooth, major surface (e.g., FIG. 3) of substrate (12). Preferably, the therapeutic substance is essentially uniformly distributed over a major portion of at least one major surface of substrate (12). Obviously, for ease of application of the therapeutic substance to a user, it is desirable to distribute the therapeutic substance over the entire portion of at least one major surface of the substrate; however, in order to effectively laminate the multi-ply layers without using adhesives (adhesives are undesirable because they may penetrate the substrate and reduce the tissue's tactile properties, such as softness), at least a minor portion of the major surfaces must be void of therapeutic substance so that those portions may be mechanically embossed. Mechanically embossing tissue plies is not an effective means of connecting substrate plies that contain therapeutic substance because the therapeutic substance inhibits effective bonding regardless of whether the therapeutic substance is applied before or after embossing. Therefore, the areas to be embossed should remain free of therapeutic substance. Since a user will most likely use the center portion of a tissue and embossing reduces the softness of the tissue, it is desirable to minimize the areas containing embossments and position the embossments such that the user has access to the therapeutic treatment on the central portion of the tissue. Thus, the preferred arrangement of embossments on the tissue, as shown in FIGS. 1 and 2, is to place the embossing regions (46) along longitudinal edges (32) so that the central portion of the tissue may contain therapeutic substance and remain soft for contacting the user. While this is a preferred configuration, it is to be understood that embossing regions (46) could exist in many configurations and combinations. A major portion of a major surface should be understood to include the entire major surface, less the embossed portions of the surface. Preferably, therapeutic substance (14) is applied to both major surfaces (20, 21) of substrate (12).

Likewise, those skilled in the art can determine the quantity of therapeutic substance to be applied to any given area of substrate (12) according to the type of medicine to be applied and the particular application involved (e.g., facial tissue, towelettes, etc.). Factors to be considered include the cost of the therapeutic substance, its physical characteristics, the quantity which should be applied to the skin to accomplish the particular goal of the application (e.g., soothing, protecting, relieving cold and allergy symptoms, providing an aesthetically pleasing physical appearance, etc.) and convenience of packaging. The preferred level of therapeutic substance on each side of the preferred substrate (12) for facial tissues is from about 0.8 $g/m^2$ to about 8 $g/m^2$.

Medicated tissue (10) is illustrated as comprising a first ply (16) and a second ply (18) which preferably are identical and comprise the layered tissue paper sheets discussed in referenced U.S. Pat. No. 4,481,243 to Allen. Medicated tissue (10) as shown in FIG. 3 has therapeutic substance (14) applied to both major portions of both major surfaces (42). Although therapeutic substance (14) is shown as a surface coating in FIGS. 1 and 2, it will be understood that the therapeutic substance often will penetrate to a greater or lesser extent through the thickness of first ply (16) and second ply (18) depending upon the rheology of the therapeutic substance and the absorbency of the substrate relative to that substance. However, therapeutic substance (14) generally will not fully impregnate or saturate first ply (16) or second ply (18) due to the inclusion of solid components which are miscible with, and can entrap, the liquid on the surface of the plies.

The solid components of the therapeutic substance can work in several ways, none of which are mutually exclusive. For example, they can form hydrogen bonds with the substrate and become localized on the surface of the plies. Also, it often is desirable to have a solid component that will quickly crystallize (i.e., solidify) at the substrate's surface during manufacture and have the highest possible viscosity within the limits of processing capabilities which prevents the therapeutic substance from substantially flowing into the interior of the paper as it cools or when shear forces are applied during use.

First and second plies (16, 18) preferably are united (i.e., laminated together) by a pattern of embossments (30) extending through embossing regions (46) adjacent to and generally parallel with longitudinal edges (32). In the embodiment of medicated tissue (10) illustrated in FIGS. 1 and 2, therapeutic substance (14) is applied substantially uniformly over major portion (42) of major surfaces (38, 40) of medicated tissue (10) essentially continuously between longitudinal edges (32). Embossing regions (46) are left substantially free of therapeutic substance (14).

An enlarged view of the pattern of embossments (30) is illustrated in FIG. 3 as a multiplicity of diamond shaped individual embossments (50) in a bilaterally staggered array of generally parallel rows. In this preferred configuration, embossments (30) are arranged in a limited area (e.g., embossing regions (46)) along oppositely disposed edges of tissue (10)) having a width of from about 0.5 to about 0.75 centimeter and extending substantially continuously along each longitudinal edge (32). The individual embossments (50) may be diamond shapes having a major point (52) to major point (52) dimension (D) from about 0.9 to about 1.1 millimeters and a minor point (54) to minor point (54) dimension (d) from about 0.4 to about 0.6 millimeter. Diamond shaped embossments (50) are spaced from about 0.4 to about 0.6 millimeter between minor points (54) in each row.

Embossing regions (46) preferably are left substantially free of therapeutic substance (14), as the presence of therapeutic substance (14) in such regions may tend to weaken the bonding effect of pattern of embossments (30).

In the preferred embodiment for facial tissue, medicated tissue (10) is from about 15 to 25 centimeters wide and from about 20 to about 25 centimeters long. The tissues are either C-folded or Z-folded, as is well known in the art.

Having shown and described the preferred embodiments of the present invention, further adaptations of the medicated tissue described herein can be accomplished by appropriate modifications by one of ordinary skill in the art without departing from the scope of the present invention. Several of such potential modifications have been mentioned, and others will be apparent to those skilled in the art. For example, the present invention can be applied to products other than facial tissue, such as toilet tissue, towelettes and the like. Accordingly, the scope of the present invention should be considered in terms of the following claims and is understood not to be limited to the details of structure and operation shown and described in the specification and drawings.

I claim:

1. A medicated tissue for applying medication to a user, comprising:

a substrate having two exposed surfaces; and a semisolid therapeutic substance comprising a lotion component transferably carried on at least one exposed surface of said substrate, such that, in use, said therapeutic substance is transferable from the substrate to said user, said therapeutic substance including solid components for preventing the therapeutic substance from fully impregnating the substrate, and thereby reducing the amount of therapeutic substance required for effective transfer to the user.

2. The tissue of claim 1 wherein said therapeutic substance comprises a lotion and a medicinal component.

3. The tissue of claim 2 wherein said medicinal component comprises material selected from the group consisting of viricides, disinfectants, and analgesics.

4. The tissue of claim 2 wherein said lotion comprises by weight from about 40% to about 60% mineral oil, from about 6% to about 14% paraffin wax, from about 15% to about 25% cetearyl alcohol from about 1% to about 5% aloe extract, and from about 5% to about 14% steareth-2.

5. The tissue of claim 2 wherein said medicinal component comprises a medicinal scent selected from the group consisting of natural menthol, synthetic menthol, and camphor.

6. The tissue of claim 2 wherein said therapeutic substance comprises about 0.25% to about 50% of said medicinal component and about 50% to about 99.75% of said lotion.

7. The tissue of claim 2 wherein said medicinal component is dispersed substantially throughout said lotion.

8. The tissue of claim 7 wherein said medicinal component is contained within partially open microcapsules for continual controlled release of said medicinal component.

9. The tissue of claim 7 wherein said medicinal component is contained within microcapsules that rupture at a point of use.

10. The tissue of claim 1 wherein said substrate comprises at least 2 plies of tissue paper, said plies being united by a pattern of embossments in an embossing region, said embossing region being substantially free of said therapeutic substance.

11. The tissue of claim 1 wherein each exposed surface of said substrate carries about 0.8 g/m$^2$ to about 8 g/m$^2$ of said therapeutic substance thereon.

12. A medicated tissue for soothing skin and relieving cold symptoms of a user, comprising:

a substrate having two exposed surfaces; and a semi-solid therapeutic substance carried on at least one exposed surface of said substrate said therapeutic substance comprising a medicinal component and a lotion component which includes solid components for preventing the therapeutic substance from fully impregnating the substrate, thereby reducing the mount of therapeutic substance required for effective transfer to the user.

13. The tissue of claim 12 wherein said medicinal component comprises a medicinal scent selected from the group consisting of natural menthol, synthetic menthol, and camphor.

14. The tissue of claim 12 where said medicinal component comprises material selected from the group consisting of viricides, disinfectants, and analgesics.

15. The tissue of claim 12 wherein said medicinal component is dispersed substantially throughout said lotion.

16. The tissue of claim 15 wherein said medicinal component is contained within microcapsules for controlled release of said medicinal component.

17. A medicated tissue for applying medication to a user, said tissue comprising:

a substrate having two exposed surfaces;

a semisolid lotion transferably carried on at least one exposed surface of said substrate, such that in use said lotion is transferable from the substrate to said user, said semi-solid lotion including solid components for preventing the lotion from fully impregnating the substrate; and a medicinal component, said medicinal component being contained within microcapsules dispersed within said lotion.

* * * * *

UNITED STATES PATENT AND TRADEMARK OFFICE
CERTIFICATE OF CORRECTION

PATENT NO. : 5,720,966
DATED : February 24, 1998
INVENTOR(S) : Ostendorf

It is certified that error appears in the above-identified patent and that said Letters Patent is hereby corrected as shown below:

Claim 4, column 8, line 1, after "alcohol" insert --,--.

Claim 12, column 8, line 31, after "substrate" insert --,--;
       column 8, line 35, change "mount" to --amount--.

Claim 14, column 8, line 42, change "where" to --wherein--.

Signed and Sealed this

Twelfth Day of May, 1998

Attest:

BRUCE LEHMAN

*Attesting Officer*     *Commissioner of Patents and Trademarks*